United States Patent
Bieser et al.

(10) Patent No.: US 7,255,882 B2
(45) Date of Patent: Aug. 14, 2007

(54) ENKEPHALINASE INHIBITOR AND GABA PRECURSOR LOADING AS ANTI-ANXIETY COMPOSITIONS

(76) Inventors: Albert Howard Bieser, 15535 St. Cloud, Houston, TX (US) 77062; Terry Leo Neher, 7151 E. Hwy. 60 #202, Gold Canyon, AZ (US) 85219

( * ) Notice: Subject to any disclaimer, the term of this patent is extended or adjusted under 35 U.S.C. 154(b) by 419 days.

(21) Appl. No.: 10/977,976

(22) Filed: Oct. 29, 2004

(65) Prior Publication Data
US 2005/0163865 A1 Jul. 28, 2005

Related U.S. Application Data

(60) Provisional application No. 60/515,363, filed on Oct. 29, 2003.

(51) Int. Cl.
| | |
|---|---|
| A61K 31/197 | (2006.01) |
| A61K 31/198 | (2006.01) |
| A61K 31/255 | (2006.01) |
| A61K 31/375 | (2006.01) |
| A61K 31/4415 | (2006.01) |
| A61K 31/4985 | (2006.01) |
| A61K 31/315 | (2006.01) |
| A61K 33/06 | (2006.01) |
| A61K 33/10 | (2006.01) |
| A61P 3/02 | (2006.01) |
| A61P 25/22 | (2006.01) |
| A61P 25/36 | (2006.01) |
| A61P 25/32 | (2006.01) |

(52) U.S. Cl. ............. 424/643; 424/602; 424/641; 424/675; 424/678; 424/681; 424/682; 424/683; 424/686; 424/687; 424/688; 424/692; 424/693; 424/696; 424/697; 424/722; 514/249; 514/251; 514/345; 514/419; 514/474; 514/494; 514/553; 514/556; 514/561; 514/563; 514/567; 514/578; 514/809; 514/811; 514/812

(58) Field of Classification Search ............... 424/602, 424/641, 643, 675, 678, 681, 682, 683, 686, 424/687, 688, 692, 693, 696, 697, 722; 514/249, 514/251, 345, 419, 474, 494, 553, 556, 561, 514/563, 567, 578, 809, 811, 812
See application file for complete search history.

(56) References Cited

U.S. PATENT DOCUMENTS

| | | | | | |
|---|---|---|---|---|---|
| 4,761,429 | A | * | 8/1988 | Blum et al. ............... | 514/561 |
| 5,189,064 | A | * | 2/1993 | Blum et al. ............... | 514/561 |
| 5,922,361 | A | * | 7/1999 | Bieser et al. .............. | 424/682 |
| 6,159,506 | A | * | 12/2000 | Bieser et al. .............. | 424/682 |
| 6,955,873 | B1 | * | 10/2005 | Blum ......................... | 435/6 |
| 2004/0116351 | A1 | * | 6/2004 | Halevie-Goldman ...... | 514/18 |

OTHER PUBLICATIONS

Medline abstract 93233833 (1993).*

* cited by examiner

*Primary Examiner*—John Pak
(74) *Attorney, Agent, or Firm*—Harrison Law Office

(57) ABSTRACT

Benzodiazepine withdrawal induced anxiety is treated by administration of an enkephalinase inhibitor, and a gamma-aminobutyric acid ("GABA") precursor, or an endorphin or enkephalin releaser. These components promote restoration of normal neurotransmitter function and are non-addictive. Use of the enkephalinase inhibitor D-phenylalanine, the GABA precursor glutamine, the serotonin precursor 5-HTP, glycine, and taurine, in combination with coenzymatic functionality of folic acid is preferred for activation of ligand-gated Cl$^-$ channel in the central nervous system. Food supplement embodiments provide the human body nutritional supplements to intake certain neurotransmitter precursor substrates, thereby enabling patients of all ages to self-regulate their ability to quell perturbations to equilibrium and simultaneously to adverse effects upon normal physiological and psychological functioning attributable to induced anxiety and panic associated with benzodiazepine withdrawal.

57 Claims, 2 Drawing Sheets

Figure 2:
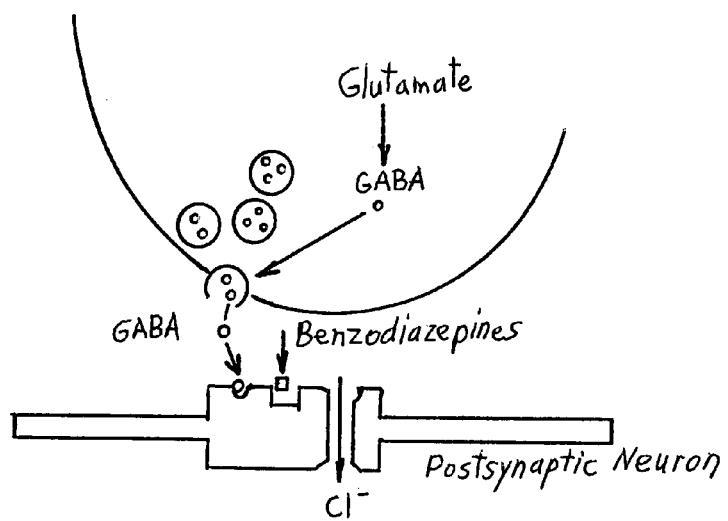

FIGURE 1: Schematic of the Formation of GABA
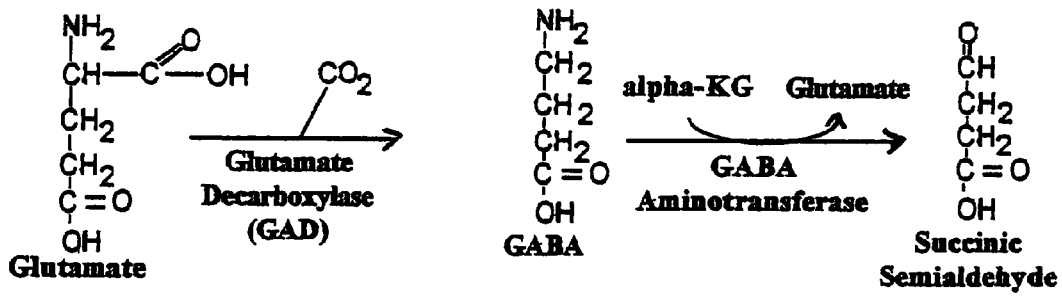
FIGURE 4: GABA Shunt and the Kreb's Cycle
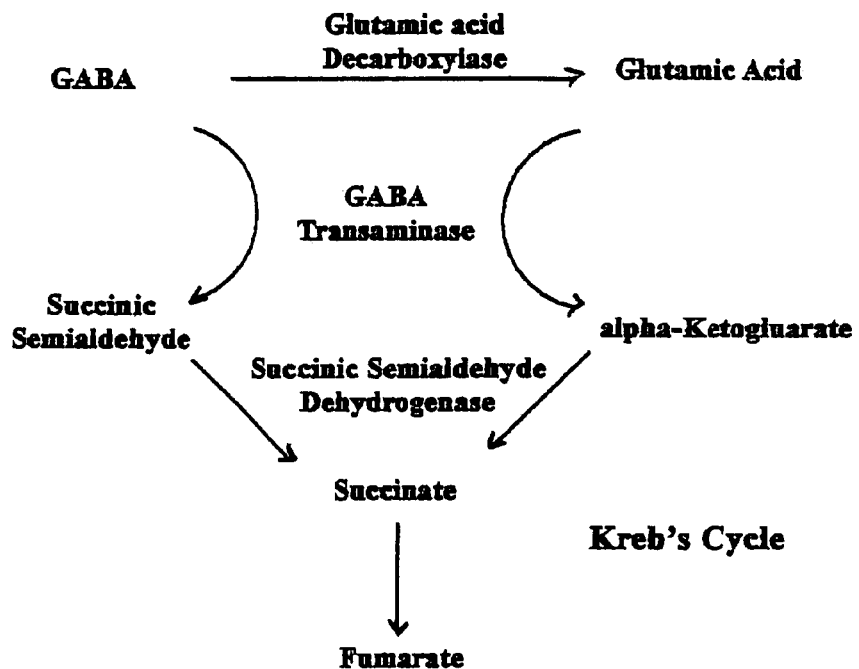

GABA Neuron

GABA-α Receptor Complex

ENKEPHALINASE INHIBITOR AND GABA PRECURSOR LOADING AS ANTI-ANXIETY COMPOSITIONS

RELATED APPLICATIONS

This application claims priority based upon Provisional U.S. Application Ser. No. 60/515,363 filed Oct. 29, 2003.

BACKGROUND OF THE INVENTION

This invention relates to dietary supplement compositions, and more particularly relates to dietary supplement compositions, which promote the ability of the human body to engender calmative conditions when subjected to induced anxiety and panic due to benzodiazepine withdrawal.

As is understood by those skilled in the art, neuroregulators are chemicals that enable messages to be transmitted among nerve cells located in the brain. Each of the several neuroregulators found in the brain transmit to a specific receptor site located throughout the human body. Such neuroregulators may be either neurotransmitters that act through synaptic transmission or neuromodulators that act through mechanisms other than synaptic transmission. For instance, responsive to stress, B-endorphin has been observed in the art to be secreted concomitantly with ACTH. Similarly, leu-enkaphalin has been observed to function as a neurotransmitter in the area of the brain involved with a reward and a sense of euphoria. As will be understood by those conversant in the art, endorphins, enkaphalins, and kappa antagonists comprise endogenous opioids—which are intertwined with the body's ability to cope with stress and other equilibrium-threats.

U.S. Pat. No. 4,439,452 teaches that enkephalins have the ability to act as analgesics when administered to various animals and humans by certain special procedures, including intracerebral injections. Only limited results have been obtained from oral administration of enkephalins, however, attributable to the destruction of the enkephalins by the action of certain enzymes, which resemble carboxypeptidase. These and other enzymes, which tend to deactivate enkephalin, are known collectively as "enkephalinase."

Blum in U.S. Pat. No. 4,761,429, teaches a composition intended to inhibit the action of enkephalinase and endorphinase. Such an enkephalinase inhibitor is a substance that tends to inhibit destruction of neuropeptides and endorphins in the animal body. More particularly, D-phenylalanine or hydrocinnamic acid—including DL-phenylalanine ("DLPA") and D-amino acids—was discovered by Blum to function as an enkephalinase inhibitor when administered as a daily dosage in range of 32 to 10,000 mg. The technique taught therein enables endorphins to be accumulated as reservoirs in regions of the nervous system and, when stressful conditions arise, for being readily dispatched from such reservoirs into the bloodstream.

A related development in the art is disclosed also by Blum, in U.S. Pat. No. 5,189,064, wherein compositions comprising an endorphinase or enkephalinase inhibitor and, optionally, a suitable precursor promote restoration of normal neurotransmitter function without side-effects. This optional precursor component may be selected from either a dopamine precursor or a serotonin precursor, a gamma-aminobutyric acid ("GABA") precursor or an endorphinase or enkephalinase precursor. Accordingly, those skilled in the art will appreciate the potential benefits derived from interaction between neurotransmitters such as dopamine, GABA, serontonin, and norepinephrine, on the one hand, and with opioid peptides such as endorphins and enkaphalins, on the other hand. Indeed, it should be evident that compositions premised upon such ingredients as d-phenyalanine and l-phenyalanine in conjunction with l-glutamine are likely to be applicable in treatment protocols for reducing drug addiction and the like.

It will be understood by those skilled in the art that, to help explain the mechanisms used by the human body to contend with challenges and threats to normal emotional and ingestive behavior, a "reward cascade" model has been suggested by K. Blum, M. C. Trachtenberg, and G. P. Kozlowski. ("Cocaine Therapy: The 'Reward Cascade' Link," Professional Counselor, January/February 1989 p.27.) This reward cascade model describes normal stimulations as originating in the hypothalamus and comprising a chain of the following events: (1) neurons in the hypothalamus release serotonin; (2) serotonin activates the opioid peptide methionine enkephalin; (3) methionine enkephalin is released at the substantia nigra and interacts to inhibit receptors controlling neuronal release of GABA; (4); dopamine thus released acts as the target messenger of reward; and (5) cells originating in the locus coeruleus and projecting into the hippothalamus release norepinephrine.

It should be understood by those skilled in the art that increased supply of dopamine is a by-product of inhibiting GABA activity, since the primary function of GABA is believed to control dopamine output in the ventral tegmental region. The cascade of events, when in equilibrium, provides homeostatic regulation of the extent of activity, according to this model. On the other hand, a perturbation to equilibrium causing a modification of feelings and/or behavior are/is effectuated if a neurotransmitter or neuromodulator either becomes dysfunctional or its corresponding receptor site becomes non-responsive.

It is also known that, based in significant part upon post-respective reports of millions of persons, primarily in the United States but also worldwide, that the advent of dependency on benzodiazepines has become epidemic and extremely difficult with which to deal. Furthermore, it is clear that long-term use of benzodiazepines have given rise to many unwanted effects, including memory problems, cognition problems, emotional blunting and depression, increasing anxiety, physical symptoms and dependence. This latterdependency, unfortunately, has not been recognized by the medical community and, indeed, has routinely been exacerbated by the continued prevalent prescriptive practices of physicians throughout the United States. Contrariwise, various medical organizations throughout the world, e.g., the Committee on Safety of Medicines, the Royal College of Psychiatrists—both located in the United Kingdom—have concluded and published the finding that benzodiazepines are unsuitable for long-term use and should, in general, be prescribed only for periods of 2-4 weeks.

The identical conclusory and warning language has been rendered as being integral to the "insert" literature by ethical pharmaceutical companies producing and distributing benzodiazepines. It has been found that most physicians, however, ignore these warnings, and exclusively direct energy and attention to responding to symptoms by patients' reports. As a result millions of persons have unwittingly used these medications to control various symptoms of anxiety and related conditions while, ironically, simultaneously developing a strong dependency upon the use of benzodiazepine.

Unfortunately, it has become abundantly clear from patients' reports that physicians typically have declined to assist patients gradually discontinue use of the benzodiazepines. It would appear, based upon this evidence, that physicians have not been trained to deal with withdrawal from drug dependency, especially drugs that have been prescribed in good faith and with curative intentions. Drug withdrawal reactions generally tend to mirror the drugs' initial effects; in the case of benzodiazepines, sudden cessation after chronic use may result in multiple, serious consequences. Among these consequences are insomnia and nightmares, increased muscle tension and muscle spasms, anxiety, panic attacks and seizures. As is known to practitioners in the art, these reactions are caused by abrupt nervous system adaptations that have occurred responsive to the chronic presence of the drug. Rapid removal of the drug results in rebound over-activity of all the systems, which have been damped by the benzodiazepine and are now no longer opposed. As a result of this rebound over-activity, the brain and peripheral nervous system are in a chronic state of hyperexcitability, and, consequentially, are susceptible to the deleterious impact of stress.

U.S. Pat. Nos. 5,922,361 and 6,159,506 disclose that protracted stress has been found to cause the human body to suffer from adverse physical and psychological affects. Indeed, as will be understood by those conversant in the art, stress has been implicated in the incidence of heart disease, hypertension, migraine headaches, ulcers, and depression. It will also be understood by those skilled in the art that, while each human body reacts somewhat differently to insults from stress, the changes that generally occur are similar.

For example, it is known among practitioners that, in the course of responding to stress, the human body suffers from a depletion of neuroregulators from each of the endogenous opioid system, gamma-aminobutyric acid ("GABA") system, and serotonin system. As another example, it is also known that the neurotransmitters dopamine, enkephalin, GABA, and norepinephrine from each of the hypothalamus and hippocampus have important affects upon anxiety disorders. Similarly, serotonin is known to also have important affects upon anxiety disorders.

Anxiety disorders, of course, are disorders associated with excessive feelings of anxiousness and nervousness. As with major depressive disorder ("MDD"), anxiety disorders are more extreme cases of what are commonly experienced at various times. A person suffering from an anxiety disorder experiences anxiety to such an extent that it significantly interferes with normal functioning; the concomitant cognitive feelings of anxiety and nervousness, neurologically translate into an overly active sympathetic nervous system. In the case of Generalized Anxiety Disorder ("GAD"), these feelings of anxiousness and nervousness are constant, as is the sympathetic activation. Not only can such feelings be unpleasant, but also can have a strong negative impact upon one's physical health. Accordingly, this type of anxiety disorder can be particularly debilitating.

Panic Disorder ("PD") also includes anxious and nervous feelings, but these feelings come and go at unanticipated times. In fact, one of the defining components of GAD and PD is that the anxiety is not due directly to any specific external stimuli. The prototypical panic attack includes many physical components such as irregular heart rate, dizziness, faintness, shortness of breath, sweating and "clamminess." All of these physical components are often associated with a general feeling of dissociation or unreality, and, in the extreme, even a feeling of impending death. A person suffering from such attacks—which come with little warning—can have significant problems in day-to-day functioning.

The treatment of anxiety disorders has developed considerably in the past 50 years. Early treatments used alcohol and barbiturates to treat anxiety, but both were associated with significant concomitant problems. This attitude and approach changed in the 1950s and 1960s, wherein the benzodiazepines were developed as effective anxiolytics. As will be appreciated by practitioners in the art, benzodiazepine-anxiolytics are still commonly used.

Benzodiazepines, work quickly and are generally well-tolerated, but may cause patients to suffer from initial sedation, ataxia, uncoordination, impaired memory and cognition; after chronic administration, they further may cause patients to suffer from physiological dependence, and thereby from withdrawal symptoms. It has been observed by practitioners that some of these adverse effects occur more frequently in older patients. Additional observations include occasional undesirable behavioral disinhibition in pediatric patients and in patients with a comorbid Cluster B Personality Disorder, e.g., patients that are antisocial, borderline, histrionic, or narcissistic.

Furthermore, people with a history of, or propensity for, alcohol or drug abuse are at risk for abusing benzodiazepines. Due to their lack of significant anti-depressant effects, these drugs are also not optimal for long-term monotherapy treatment of GAD patients or patients suffering from other anxiety disorders. As a result, there has been continual searching for new anxiolytic agents. For some anxiety disorders, tricyclic antidepressants ("TCA"s) and monoamine oxidase inhibitors ("MAOI"s) proved to be effective treatment. Unfortunately, prevalent application thereof was limited by side-effects especially during long-term therapy. During the past several years, selective serotonin re-uptake inhibitors ("SSRI") have become primary monotherapy for anxiety disorders, being better-tolerated and affording a broader spectrum of efficacy than older agents. It will be appreciated that benzodiazepines are now recommended to patients as adjunctive treatment for anxiety disorders and as monotherapy for patients who are intolerant of or unresponsive to other agents.

It is known by those skilled in the art that the most prominent affect of benzodiazepines is anti-anxiety; accordingly, nearly all acute withdrawal symptoms are characterized by anxiety and related disorders. These symptoms include psychological and physical conditions such as hypersensitivity to sensory stimuli and perceptual disorders, i.e., feeling of motion, impressions of walls or floors tilting, sensation of walking on cotton, etc. In addition, and perhaps most debilitating, is the incidence of de-personalization, feelings of unreality, peripheral neuropathy, i.e., tingling and numbness in extremities, visual hallucinations, distortion of body image, muscle-twitching and weight-loss.

Benzodiazepines function by enhancing the binding qualities of the GABA neurotransmitter, considered by practitioners to be the major calming influence in the brain and body. This GABA neurotransmifter is found in almost every region of the brain and is formed through the activity of the enzyme glutamic acid decarboxylase ("GAD"); GAD is known to function as a catalyst for formation of GABA from glutamic acid. This synthesis of GABA has been linked to the Kreb's cycle. GAD requires vitamin $B_6$ (pyridoxal phosphate) as a cofactor, which can be used to regulate the levels of GABA.

Following release, GABA can be taken back up or recycled by the neurons or by astrocytes. It appears that the release of GABA is also under auto-receptor control. GABA can be metabolized by a trans-amination reaction with alpha keto-glutarate, catalyzed by GABA-transaminase ("GABA- T") to form succinic acid semi-aldehyde. Succinic acid semi-aldehyde is metabolized further to succinic acid which is also a Kreb's cycle intermediate. See FIGS. 1 and 4.

It is known in the art there are two basic GABA receptors, GABA-a and GABA-b. GABA-a is prevalent in the mammalian brain; 60-75% of all synapses in the central nervous system ("CNS") are GABAergic. The GABA-a receptor is similar to the acetylcholine receptor since it is related to an ion channel; binding GABA to this receptor increases the permeability to chloride ions ($Cl^-$), thereby causing hyperpolarization of the neuron. The GABA-a receptor has four basic subunits—2 alpha and 2 beta peptides—which surround a chloride channel. There are three basic binding sites on this complex: (1) GABA site; (2) benzodiazepine site per FIG. 3; and (3) the channel which is essentially a barbiturate site. Binding to the benzodiazepine site can have three affects: (1) agonism; (2) inverse agonism; or (3) antagonism.

As a result of GABA primary site-binding, in conjunction with secondary sites, being activated by benzodiazepine, chloride channels are opened thereby enabling chloride ions to enter the excitatory neuron and to reduce neuron-firing. See, FIG. 2. It will be understood that this action effects reduced excitation in the implicated system and engenders a "calming" effect upon the patient. When secondary sites are continually activated by an outside source by a drug such as a benzodiazepine, this effects a reduction in the available GABA. Thus, to be calmed, the excitatory system will require increasing amounts of secondary transmitter function which effects a benzodiazepine-dependency in order to reduce excitability or anxiety.

After release into the synapse, free GABA that does not bind to either the GABA-a or GABA-b receptor complexes can be taken up by neurons and glial cells. Four different membrane transporter proteins, known as GAT-1, GAT-2, GAT-3, and BGT-1, which differ in their distribution in the CNS, are believed to mediate the uptake of synaptic GABA into neurons and glial cells.

The GABA-a receptor subtype regulates neuronal excitability and rapid changes in fear arousal, such as anxiety, panic, and acute stress response. Drugs that stimulate GABA-a receptors, such as benzodiazepines and barbiturates, have anxiolytic and anti-seizure effects via GABA-a-mediated reduction of neuronal excitability, which effectively raises the seizure threshold. Findings that GABA-A antagonists produce convulsions in animals and that there is decreased GABA-a receptor binding in positron emission tomography ("PET") study of patients with panic disorder support the anti-convulsant and anxiolytic effects of the GABA-a receptor. In addition, low plasma GABA has been reported by practitioners in the art in some depressed patients and may even serve as a trait marker for mood disorders.

Importantly, when benzodiazepine is withdrawn after five to seven days, a patient is often left with symptoms of generalized anxiety disorder and may even experience panic attacks. These symptoms are believed to be due to an insufficient level of transmitters prerequisite for facilitating chloride ion conductance. The neuron continues to fire the excitatory message and there are literally tens of thousands messages that are being sent simultaneously. This unabated firing of norepinepherine neurons, for example, produces the physical and psychological sensations that have been termed "anxiety."

It will be appreciated that the issue then devolves to how to effectively manage anxiety symptoms. Although useful for treating craving disorders including cocaine addiction and the like, the approaches taught by the Blum compositions and methodology are limited to applying nutritional supplements on pro re nata basis, i.e., p.r.n. Heretofore, unknown in the art is a dietary supplement which provides the benefits of the teachings of Blum—for mitigating the adverse affects of the human body being regularly subjected to stressful assaults—on a self-regulating basis wherein a sufficient repository of neurotransmitters and the like is generally available for assuaging perturbations from normal physiological and psychological functions. That is, unlike a formal treatment program for anxiety under which medication or dietary supplements are prescribed as needed on a patient-by-patient basis, it would be advantageous for patients to enjoy the benefit of an available daily dosage of a food supplement that provides a means for routinely attenuating benzodiazepine-withdrawal-induced anxiety, and other physiological and psychological function impairments.

It will be understood that chronic benzodiazepines are inappropriate for administration in such individuals. While selective serotonin re-uptake inhibitors ("SSRI"s) and selective norepinephrine re-uptake inhibitors ("SNRI"s) can be helpful, people with substance abuse problems generally do not sufficiently benefit from these drugs. Indeed, these individuals tend to experience more side effects from anti-depressants than individuals without abuse problems.

Accordingly, these limitations and disadvantages of the prior art are overcome with the present invention, wherein improved compositions are provided which are particularly useful in reducing the effects of anxiety without the necessity for prescribing medication or for providing food supplements on a p.r.n. basis.

SUMMARY OF THE INVENTION

The present invention provides food supplement compositions specially formulated for coping with induced anxiety and panic due to benzodiazepine withdrawal. More particularly, compositions taught by the present invention combine suitable precursor substrates and the like $B_6$, whereby gamma-aminobutyric acid (hereinafter abbreviated "GABA") is produced in sufficient quantity. As will be appreciated by those conversant with the art, this GABA tends to accumulate within the human central nervous system (hereinafter abbreviated "CNS"), thereby increasing the levels of GABA. As will hereinafter be described in detail, it will also be appreciated that by thus increasing GABA levels, the human body benefits from a self-regulating faculty for coping with anxiety and panic assaults upon physiological and psychological equilibrium.

For enabling the human body to self-regulate its defenses to continual stressful assaults, the present invention provides the hypothalamus with a means for preventing significant perturbation or instability to feedback loops associated with dopamine production by assuring sufficiently increased levels of endogenous opioids. U.S. Pat. Nos. 5,922,361 and 6,159,506 teach a coenzymatic mechanism in which folic acid effectively accelerates the transformation of a substrate primarily comprising D-phenylalanine, L-glutamine, and L-tryptophan to met-enkephalin end product.

According to the teachings of the present invention, a methodology has been discovered which supplements the nutritional intake of certain neurotransmitter precursor substrates, thereby enabling patients of all ages to be equipped with the ability to routinely quell adverse affects upon their normal physiological and psychological functioning while simultaneously quelling induced anxiety and panic due to benzodiazepine withdrawal.

It is accordingly an object of the present invention to provide food supplements and a concomitant methodology for enabling the human body to self-regulate its ability to quell perturbations to its equilibrium due to induced anxiety and panic due to benzodiazepine withdrawal.

It is also an object of the present invention to provide food supplement compositions for providing the human body sufficient resources for avoiding unstable physiological and psychological effects attributable to effects of induced anxiety and panic due to benzodiazepine withdrawal.

It is also an object of the present invention to provide food supplement compositions comprising surprisingly low quantities of suitable neurotransmitter precursor substrate.

It is another object of the present invention to provide food supplement compositions produced from neurotransmitter precursor substrate using a folic acid coenzyme.

It is a further object of the present invention to provide a method for eliminating adverse effects upon the human body's systems caused by homocysteine, by promoting the conversion of L-homocysteine to L-methionine.

These and other objects and features of the present invention will become apparent from the following detailed description, wherein reference is made to illustrative examples and related tables and to the figures in the accompanying drawings.

IN THE DRAWINGS

Figure 3:
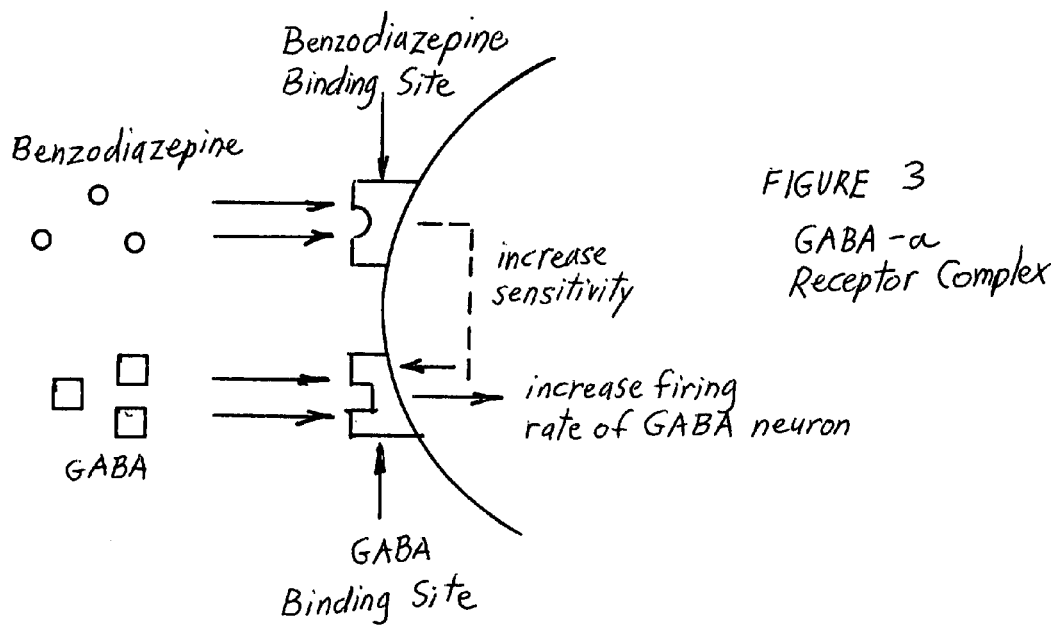

FIG. 1 depicts a schematic of the formation of GABA.
FIG. 2 depicts a GABA neuron.
FIG. 3 depicts GABA-a Receptor Complex.
FIG. 4 depicts the relationship between GABA and the Kreb's Cycle.

DETAILED DESCRIPTION

The food supplement compositions contemplated by the present invention have been developed based upon the teachings of Blum et al. disclosed in U.S. Pat. Nos. 4,761,429 and 5,189,064, which are incorporated herein by reference. As will be hereinafter described in detail, the present invention provides nutrition supplements that assure the human body of having sufficient neurotransmitter precursors and the like to enable assaults from stressful circumstances and conditions to be accommodated by self-regulation. Thus, as will be understood by those skilled in the art, embodiments of the present invention avoid the necessity of prescribing a conventional post-stress regimen of medications or nutritional supplements administered on a p.r.n. basis. That is, the food supplement compositions taught by the present invention provide a means and method for accumulating sufficient opioid concentrations in the human body for safely coping with prevalent conditions of stress.

It has been discovered that incorporating suitable quantities of folic acid into compositions taught by Blum to inhibit breakdown of endogenous substances such as enkaphalins and endorphins, provide a reliable and cost-effective means for assuring that the human body has sufficient opioid resources to quell common stressful assaults upon its normal physiological and psychological functioning. More particularly, including a folic acid dosage of from 50-150 micrograms in embodiments of the present invention has been discovered to enable a combination of the Blum prescribed precursor ingredients comprising D-phenylalanine, L-glutamine, and Vitamin $B_6$ in amounts heretofore unknown in the art. As will be hereinafter described in detail, corresponding to this preferred folic acid dosage, it has been found that a daily dosage thereof from 50-900 milligrams (mg) provides a cofactor or coenzyme prerequisite for the stress-accommodating capabilities of the present invention. Moreover, as will be understood by those skilled in the art, this folic acid cofactor accomplishes the performance suggested by Blum et al. at surprisingly low concentrations of component precursors.

Contrary to the methodology heretofore practiced in the art, wherein dosage is prescribed on a p.r.n. basis, the present invention contemplates compositions which are applicable in dosages generally administered on the basis of a patient's age. For example, U.S. Pat. No. 4,761,429 specifically states that the broad range of dosage shown in the various examples is intended to compensate for genetic variability and human specific pharmogenetic response. As an example, the dosage disclosed for D-phenylalanine ranges from 16 to 500 mg, with a daily dosage ranging from 16 to 5,000 mg. Similarly, the dosage for L-glutamine ranges from 25 to 500 mg, with a daily dosage ranging from 25 to 5,000 mg. It should be evident that the only practicable way to administer the anti-craving treatment and the like is on a patient-by-patient basis.

The present invention, on the other hand, generally teaches narrower dosage ranges. In particular, D-phenylalanine ranges from 1 to 10 mg, with a daily dosage ranging from 5 to 30; L-glutamine ranges from 1 to 75 mg, with a daily dosage ranging from 50 to 300 mg; glycine ranges from 1 to 75 mg, with a daily dosage ranging from 50 to 300 mg; taurine ranges from 1 to 50 mg, with a daily dosage ranging from 50 to 300 mg; 5-HTP ranges from 1 to 75 mg, with a daily dosage ranging from 10 to 100 mg; Vitamin $B_6$ from 1 to 75 mg, with a daily dosage ranging from 1 to 75 mg. Folic acid is included in this formulation in a dosage of 0.13 mg, with a daily dosage of 2 mg, to promote oxidation in the blood as a hematopoietic agent. U.S. Pat. No. 6,159,506, teaches that folic acid provides a crucial, enzymatic function in production of endrogenous opioids as an ingredient of food supplement compositions.

Further comparison with the compositions contemplated by Blum in U.S. Pat. No. 5,189,064 clearly indicates that the compositions of the present invention may be effectuated on a self-regulating basis. Each of the ingredients of the Blum compositions disclosed therein may vary by an order of magnitude contemplated to be from 10-1,000%. As an example of an amino acid formulation taught thereunder, the dosage disclosed for DL-phenylalanine is 250 mg, with a daily dosage of 1500 mg; the dosage disclosed for L-tyrosine is 150 mg, with a daily dosage of 900 mg. Similarly, the dosage for L-glutamine is 50 mg, with a daily dosage of 300 mg. Folic acid is included in this formulation in a dosage of 60 mg, with a daily dosage of 400 mg.

As is well known in the art, two significant characteristics of enzymes are high catalytic efficiency and high degree of specificity for substrates. A single enzyme may react with only a single substrate or, in some instances, may react with a particular chemical grouping of chemically related substrate. It is understood in the art that enzyme molecules are efficient vehicles for accelerating transformation of substrate to end product. For instance, a single enzyme molecule may effect the change of as many as 10,000 to 1 million molecules of substrate per minute. This ability, together with the fact that enzymes are not consumed or altered during consequent catalytic reactions, reveals why vanishingly small quantities of enzymes are sufficient for cellular processes.

Enzymes comprise proteins or proteins combined with other chemical groups. Many enzymes consist of a protein combined with a low-molecular weight organic molecule referred to as a coenzyme or cofactor. The essential component of several coenzymes has been found to be a vitamin. Several B-vitamins, including thiamine ($B_1$), riboflavin ($B_2$), niacin ($B_3$), pyridoxine ($B_6$), and folic acid have been identified as the primary components of coenzymes. As will be evident to those skilled in the art, the coenzymatic functionality of folic acid for use in U.S. Pat. Nos. 5,922,361 and 6,159,506 compositions known in the art in synergistic combination with GABA precursor loading, glycine and taurine loading for activation of ligand-gated $Cl^-$ channel underlies a novel aspect of the present invention.

According to the present invention, properly combining precursor substrates for GABA loading, glycine and taurine loading for activation of ligand-gated $Cl^-$ channel in the CNS and the coenzyme effect of folic acid, produce a sufficient reduction in the negative symptoms associated with benzodiazepine withdrawal. As will be appreciated by those conversant with the art, these components promote restoration of normal neurotransmitter function and are non-addictive.

Neurotransmitter transport systems are integral to the release, re-uptake and recycling of neurotransmitters at synapses. High affinity transport proteins found in the plasma membrane of pre-synaptic nerve terminals and glial cells are responsible for the removal from the extracellular space of released-transmitters, thereby terminating their actions. Plasma membrane neurotransmitter transporters fall into two structurally and mechanistically distinct families. The majority of such transporters constitute an extensive family of homologous proteins that derive energy from the co-transport of $Na^+$ and $Cl^-$, in order to transport neurotransmitter molecules into the cell against their concentration gradient. This family has a common structure of 12 presumed trans-membrane helices and includes carriers for GABA, noradrenaline/adrenaline, dopamine, serotonin, proline, glycine, choline and taurine. They are structurally distinct from the second more-restricted family of plasma membrane transporters, which are responsible for excitatory amino acid transport. The second family of transporters combine or couple glutamate and aspartate uptake to the co-transport of $Na^+$ and the counter-transport of $K^+$, with no apparent dependence on $Cl^-$. In addition, both of these transporter families are distinct from vesicular neurotransmitter transporters.

As will be understood by those skilled in the art, sequence analysis of the $Na^+/Cl^-$ neurotransmitter superfamily reveals that it can be divided into four subfamilies, constituting transporters for monoamines, the amino acids proline and glycine, GABA, and a group of orphan transporters.

Glycine is known in the art to serve two contrasting roles as a CNS neurotransmitter. First, glycine functions as an inhibitory neurotransmitter in the spinal cord, brainstem and retina, thereby activating a ligand-gated $Cl^-$ channel. Second, it is an obligatory co-agonist for activating the N-methyl-D-aspartate ("NMDA") receptor; but, unless glycine is also bound to the NMDA receptor, glutamate cannot activate this ion channel. Not surprisingly, then, as will be appreciated by those skilled in art, plasma membranes possess glycine transporters for regulating its concentration. Two independent genes have been identified that encode $Na^+$ and $Cl^-$—coupled glycine transporters—whose products, referred to as GLYT-1 and GLYT-2, have differing CNS distribution patterns, suggesting that they may, in turn, serve unique functions. Indeed the distribution of the GLYT-1 transporter suggests it may participate in regulating glycine concentrations in brain regions containing glycine-dependent NMDA receptors. Three different mRNA isoforms for GLYT-1 have been detected, which arise as a result of differential splicing or the usage of multiple promoter sites; encoding transporters of 633, 638 and 692 amino acid residues. All three of these transporters of 633, 638 and 692 amino acid residues have 50-60% similarity to other transporters in the $Na^+$ and $Cl^-$—coupled neurotransmitter transporter superfamily.

It will be appreciated by those skilled in the art that benzodiazepine withdrawal is associated with uncontrolled muscle spasms. In seizure studies of epileptic patents, increased levels of GABA, glycine and taurine were released into the CNS. Indications are that increased levels of GABA, glycine and taurine were released into the hippocampus during kainic acid ("KA") induced epilepsy and by traditional acupuncture. Recent microdialysis studies of excitatory and inhibitory amino acids, including glutamate, aspartate and taurine associated with paroxysmal hippocampal activity have found significant increases in the hippocampus of post-seizure epileptic patents. It will also be understood by those skilled in the art that evidence has shown that sodium valporate ("VPA") mechanism of action in the therapy of epilepsy is based on the phenomena of interaction with GABA and taurine. The direct application of taurine in experimental and human epilepsy was initiated more than 30 years ago and, to those conversant in the art, taurine has been known to possesses some mild anti-convulsant activity in both human and experimental animal models.

Hence, unlike the prior art, the present invention teaches precursor compositions that incorporate folic acid therein in order to effectively coordinate the effect of methionine, GABA precursor loading, glycine and taurine activation of ligand-gated $Cl^-$ channel in the CNS and the Blum ensemble of phenylalanine components to yield met-enkaphalin and GABA by the body's self-regulation faculties. This approach, of course, wherein the human body essentially produces prerequisite enkephalin to ward off stressful assaults and the like is readily distinguished from the approach taught by Blum in U.S. Pat. Nos. 4,761,429 and 5,189,064 incorporated herein by reference, wherein endorphinase and enkaphalinase inhibitors are applied on a p.r.n. basis.

A blind, placebo controlled clinical study, provided additional experimental support of the present invention, which was performed during a six-month period. Thirty-five participants from all regions of the United States volunteered to take part in a study of a supplement formulation incorporating folic acid, GABA precursor loading, glycine and taurine activation of ligand-gated $Cl^-$ channel in the CNS and the Blum ensemble of phenylalanine components to yield met-enkaphalin and GABA by the body's self-regulation faculties described herein. As will be appreciated by those skilled in the art, all participants had been taking a benzodiazepine prescribed by a physician for a minimum of 1 year and up to 10 years, and had attempted to stop the use thereof but had been unsuccessful due to overwhelming withdrawal symptoms. Each participant expressed that he was experiencing extreme discomfort to the point that his life had been significantly interrupted, frequently, even to the extent of loss of family due to withdrawal-related side-effects and degraded behavior and/or job-loss attributable to inability to function.

Furthermore, participants were questioned via telephone and asked to rate a variety of symptoms commonly identified with GAD on a scale of 1 to 10. To initiate this study, participants were randomly assigned either to the placebo group or to the experimental group. After 30 days each participant was again asked to rate the severity of withdrawal symptoms. Each 30 days the participants were asked to rate the severity of the same symptoms. None of the participants indicated that the placebo reduced any symptom to any discernable degree. However, 96% indicated that symptoms of withdrawal were positively impacted and reduced when taking the experimental formulation.

After 4 months, the participants began to indicate they knew when they were taking product and, those that were being administered the placebo, refused to continue to do so. All participants were followed for 60 days following the end of the clinical trial and were successfully continuing to taper the use of their benzodiazepine without debilitating withdrawal symptoms.

In the formulations contemplated under the present invention, D-phenylalanine ranges from 1 to 10 mg, with a daily dosage ranging from 5 to 30; L-glutamine ranges from 1 to 75 mg, with a daily dosage ranging from 50 to 300 mg; glycine ranges from 1 to 75 mg, with a daily dosage ranging from 50 to 300 mg; taurine ranges from 1 to 50 mg, with a daily dosage ranging from 50 to 300 mg; 5-HTP ranges from 1 to 75 mg, with a daily dosage ranging from 10 to 100 mg; Vitamin $B_6$ from 1 to 75 mg, with a daily dosage ranging from 1 to 75 mg; and Vitamin C from 10 to 75 mg, with a daily dosage ranging from 50 to 300 mg. Folic acid is preferably included in these formulations in a dosage of 0.13 mg, with a daily dosage of 2 mg; calcium ranges from 15 to 75 mg, with a daily dosage ranging from 50 to 150 mg; magnesium ranges from 25 to 75 mg, with a daily dosage ranging from 50 to 300 mg; and zinc ranges from 1 to 30 mg, with a daily dosage ranging from 10 to 60 mg.

Thus, it is an advantage and feature of the present invention that supplementation of the human body's precursors for producing a sufficient supply of GABA, glycine and taurine in the hypothalamus is provided. In particular, preferred compositions taught by the present invention are enumerated in Table 1.

TABLE 1

| Component | Preferred (mg) | More Preferred (mg) | Most Preferred (mg) |
| --- | --- | --- | --- |
| Folio Acid | 0.05-0.13 | 0.09-0.13 | 0.13 |
| D-Phenylalanine | 1-7 | 2-5 | 5 |
| Glycine | 10-60 | 20-50 | 50 |
| Taurine | 10-50 | 20-50 | 50 |
| L-Glutamine | 10-60 | 20-50 | 50 |
| Vitamin $B_6$ | 2-10 | 5-10 | 10 |
| Vitamin C | 10-50 | 20-50 | 50 |
| Zinc | 2-10 | 5-10 | 10 |

These embodiments of the formulations taught by the present invention, in conjunction with blending and manufacturing techniques well known in the art, consistently produce food supplement compositions that provide advantageous anxiety relief reinforcements for the human body as hereinbefore described because of the cumulative effect of each stepwise improvement. It will be readily appreciated by those skilled in the art that these components promote restoration of normal neurotransmitter function and are non-addictive.

Compositions also contemplated by the present invention are shown in Table 2, wherein a tripartite subcomposition comprising calcium, magnesium, and 5-HTP, is used. It has been found that embodiments enumerated in both Tables 1 and 2 are constituted to achieve the panoply of anxiety-relief benefits taught herein.

TABLE 2

| Component | Preferred (mg) | More Preferred (mg) | Most Preferred (mg) |
| --- | --- | --- | --- |
| Folic Acid | 0.05-0.13 | 0.09-0.13 | 0.13 |
| D-Phenylalanine | 1-7 | 2-5 | 5 |
| Glycine | 10-60 | 20-50 | 50 |
| Taurine | 10-50 | 20-50 | 50 |
| L-Glutamine | 10-60 | 20-50 | 50 |
| Vitamin $B_6$ | 2-10 | 5-10 | 10 |
| Vitamin C | 10-50 | 20-50 | 50 |
| 5-HTP | 2-10 | 5-10 | 10 |
| Calcium | 5-25 | 10-25 | 25 |
| Magnesium | 10-50 | 25-50 | 50 |
| Zinc | 2-10 | 5-10 | 10 |

The typical dosage of embodiments of the present invention to afford the human body to self-regulate its defenses to anxiety attacks and the like depends generally, of course, upon the age of the patient. For example, for 3 year old patients, a dosage of up to ½ capsule would be recommended; for 4 or 5 year old patients, a dosage of up to 1 capsule would be recommended; for 6 or 7 year old patients, a dosage of up to 2 capsules would be recommended; for 8 or 9 year old patients, a dosage of up to 3 capsules would be recommended. As will be understood by those skilled in the art, by simply extending these recommended dosages for a 16 year old or an adult, a dosage of up to 6 capsules would be recommended. It will be appreciated that the present invention provides fail-safe compositions since all of the ingredients incorporated therein are water-soluble.

The present invention further includes the following two compositions. A food supplement composition for providing a human body an ability to accumulate a sufficient supply of gamma-aminobutyric acid in the central nervous system for self-regulating its benzodiazepines which are available for contending with anxiety and panic assaults, said food supplement composition comprising: about 10 mg to about 75 mg of Vitamin C; about 1 mg to about 75 mg of Vitamin $B_6$; about 1 mg to about 30 mg of zinc; a neurotransmitter substrate consisting essentially of: about 1 mg to about 10 mg of D-phenylalanine; about 1 mg to about 75 mg of glycine; about 1 mg to about 75 mg of L-glutamine; about 1 mg to about 50mg of taurine; and from about 0.05 mg to about 0.15 mg of folic acid for coenzymatically converting said neurotransmitter substrate into met-enkephalin. A food supplement composition for providing a human body an ability to accumulate a sufficient supply of gamma-aminobutyric acid in the central nervous system for self-regulating its benzodiazepines which are available for contending with anxiety and panic assaults, said food supplement composition comprising: about 10 mg to about 75 mg of Vitamin C; about 1 mg to about 75 mg of Vitamin $B_6$; about 1 mg to about 30 mg of zinc; a neurotransmitter substrate consisting essentially of: about 1 mg to about 10 mg of D-phenylalanine; about 1 mg to about 75 mg of glycine; about 1 mg to about 75 mg of L-glutamine; about 1 mg to about 50 mg of taurine; and a combination of about 5 mg to about 75 mg of calcium, about 10 mg to about 75 mg of magnesium, and about 1 mg to about 75 mg of 5-HTP; and from about 0.05 mg to about 0.15 mg of folic acid for coenzymatically converting said neurotransmitter substrate into met-enkephalin.

Since the largest size capsule that most children are willing to swallow is a single-ought ("0") and since most adults have difficulty swallowing a double-ought ("00") size capsule, a single ought capsule can hold only about 650 mg of amino acids or metals. It should be understood that, if one of the component ingredients is present in a higher concentration than depicted in the "most preferred" column shown in either Table 1 or Table 2, then another component must be reduced by a like amount.

It is an advantage and feature of the present invention that less costly compositions may be prepared than otherwise has been available in the art. As has been hereinbefore described, not only are relatively low concentrations of such costly ingredients such as D-phenylalanine required under embodiments of the present invention, but also prohibitively expensive ingredients such as methionine are not required. Although costs of these ingredients vary according to market conditions, a typical cost-range for D-phenylalanine is $200-$300 per kg; and for L-methionine, $500-$1,000 per kg. Of course, as will be readily understood by those conversant in the art, the compositions taught by Blum did not include L-methionine because of the prohibitive price thereof.

It is contemplated that the methodology taught by the present invention, wherein the human body is given the resources to self-regulate its available supply of endogenous opioids, affords a surprisingly effective and inexpensive manner in which to mitigate the impact of frequent stressful assaults thereupon. Such an approach for providing ample precursors to enable supplementing the body's ability to manufacture prerequisite met-ekaphalins and the like has been hereinbefore unknown in the art.

Other variations and modifications will, of course, become apparent from a consideration of the specific embodiments and illustrative examples hereinbefore described. Accordingly, it should be clearly understood that the present invention is not intended to be limited by the particular disclosure herein, and embodiments and examples hereinbefore described and depicted in the accompanying drawings, but that the present invention should be measured by the scope and breadth of applicability of the underlying concepts and concomitant methodology.

What is claimed is:

1. A food supplement composition for providing a human body an ability to accumulate a sufficient supply of gamma-aminobutyric acid in the central nervous system for self-regulating its benzodiazepines which are available for contending with anxiety and panic assaults, said food supplements composition comprising:
   about 10 mg to about 75 mg of Vitamin C;
   about 1 mg to about 75 mg of Vitamin $B_6$;
   about 1 mg to about 30 mg of zinc;
   a neurotransmitter substrate consisting essentially of:
      about 1 mg to about 10 mg of D-phenylalanine;
      about 1 mg to about 75 mg of glycine;
      about 1 mg to about 75 mg of L-glutamine;
      about 1 mg to about 50 mg of taurine; and
   from about 0.05 mg to about 0.15 mg of folic acid for coenzymatically converting said neurotransmitter substrate into met-enkephalin.

2. The composition of claim 1, wherein said folic acid consists of from about 0.05 mg to about 0.13 mg.

3. The composition of claim 1, wherein said folic acid consists of from about 0.09 mg to about 0.13 mg.

4. The composition of claim 3, wherein said folic acid consists of about 0.13 mg.

5. The composition of claim 1, wherein said D-phenylalanine consists of from about 2 mg to about 7 mg.

6. The composition of claim 1, wherein said D-phenylalanine consists of from about 2 mg to about 5 mg.

7. The composition of claim 6, wherein said D-phenylalanine consists of about 5 mg.

8. The composition of claim 1, wherein said glycine consists of from about 10 mg to about 60 mg.

9. The composition of claim 1, wherein said glycine consists of from about 20 mg to about 50 mg.

10. The composition of claim 9, wherein said glycine consists of about 50 mg.

11. The composition of claim 1, wherein said L-glutamine consists of from about 10 mg to about 60 mg.

12. The composition of claim 11, wherein said L-glutamine consists of from about 20 mg to about 50 mg.

13. The composition of claim 12, wherein said L-glutamine consists of about 50 mg.

14. The composition of claim 1, wherein said taurine consists of from about 20 mg to about 50 mg.

15. The composition of claim 14, wherein said taurine consists of about 50 mg.

16. The composition of claim 1, wherein said zinc consists of from about 2 mg to about 10 mg.

17. The composition of claim 1, wherein said zinc consists of from about 5 mg to about 10 mg.

18. The composition of claim 17, wherein said zinc consists of about 10 mg.

19. The composition of claim 1, wherein said Vitamin C consists of from about 10 mg to about 50 mg.

20. The composition of claim 1, wherein said Vitamin C consists of from about 20 mg to about 50 mg.

21. The composition of claim 20, wherein said Vitamin C consists of about 50 mg.

22. The composition of claim 1, wherein said Vitamin $B_6$ consists of from about 2 mg to about 10 mg.

23. The composition of claim 1, wherein said Vitamin $B_6$ consists of from about 5 mg to about 10 mg.

24. The composition of claim 23, wherein said Vitamin $B_6$ consists of about 10 mg.

25. A food supplement compositions for providing a human body an ability to accumulate a sufficient supply of gamma-aminobutyric acid in the central nervous system for self-regulating its benzodiazepine which are available for contending with anxiety and panic assaults, said food supplements composition comprising:
   about 10 mg to about 75 mg of vitamin C;
   about 1 mg to about 75 mg of vitamin $B_6$;
   about 1 mg to about 30 mg of zinc;
   a neurotransmitter substrate essentially consisting of:
      about 1 mg to about 10 mg of D-phenylalanine;
      about 1 mg to about 75 mg of glycine;
      about 1 mg to about 75 mg of L-glutamine;
      about 1 mg to about 50 mg of taurine; and
      a combination of about 25 mg to about 100 mg of calcium, about 10 mg to about 75 mg of magnesium, and about 1 mg to 75 mg of 5-HTP; and
   from about 0.05 mg to about 0.15 mg of folic acid for coenzymatically converting said neurotransmitter substrate into met-enkephalin.

26. The composition of claim 25, wherein said folic acid consists of from about 0.05 mg to about 0.13 mg.

27. The composition of claim 25, wherein said folic acid consists of from about 0.09 mg to about 0.13 mg.

28. The composition of claim 27, wherein said folic acid consists of about 0.13 mg.

29. The composition of claim 25, wherein said D-phenylalanine consists of from about 2 mg to about 7 mg.

30. The composition of claim 25, wherein said D-phenylalanine consists of from about 2 mg to about 5 mg.

31. The composition of claim 30, wherein said D-phenylalanine consists of about 5 mg.

32. The composition of claim 25, wherein said glycine consists of from about 10 mg to about 60 mg.

33. The composition of claim 25, wherein said glycine consists of from about 20 mg to about 50 mg.

34. The composition of claim 33, wherein said glycine consists of about 50 mg.

35. The composition of claim 25, wherein said L-glutamine consists of from about 10 mg to about 60 mg.

36. The composition of claim 25, wherein said L-glutamine consists of from about 20 mg to about 50 mg.

37. The composition of claim 36, wherein said L-glutamine consists of about 50 mg.

38. The composition of claim 25, wherein said taurine consists of from about 20 mg to about 50 mg.

39. The composition of claim 38, wherein said taurine consists of about 50 mg.

40. The composition of claim 25, wherein said 5-HTP consists of from about 2 mg to about 10 mg.

41. The composition of claim 25, wherein said 5-HTP consists of from about 5 mg to about 10 mg.

42. The composition of claim 41, wherein said 5-HTP consists of about 10 mg.

43. The composition of claim 25, wherein said zinc consists of from about 2 mg to about 10 mg.

44. The composition of claim 25, wherein said zinc consists of from about 5 mg to about 10 mg.

45. The composition of claim 44, wherein said zinc consists of about 10 mg.

46. The composition of claim 25, wherein said calcium consists of from about 5 mg to about 25 mg.

47. The composition of claim 25, wherein said calcium consists of from about 10 mg to about 25 mg.

48. The composition of claim 47, wherein said calcium consists of about 25 mg.

49. The composition of claim 25, wherein said magnesium consists of from about 10 mg to about 50 mg.

50. The composition of claim 25, wherein said magnesium consists of from about 25 mg to about 50 mg.

51. The composition of claim 50, wherein said magneium consists of about 50 mg.

52. The composition of claim 25, wherein said Vitamin C consists of from about 10 mg to about 50 mg.

53. The composition of claim 25, wherein said Vitamin C consists of from about 20 mg to about 50 mg.

54. The composition of claim 53, wherein said Vitamin C consists of about 50 mg.

55. The composition of claim 25, wherein said Vitamin $B_6$ consists of from about 2 mg to about 10 mg.

56. The composition of claim 25, wherein said Vitamin $B_6$ consists of from about 5 mg to about 10 mg.

57. The composition of claim 56, wherein said Vitamin $B_6$ consists of about 10 mg.

\* \* \* \* \*